United States Patent [19]

Francis

[11] 4,329,367
[45] May 11, 1982

[54] 1-(ARALKOXYPHENYL)-2-(BIS-ARYLALKYLAMINO)-ALKANES

[75] Inventor: John E. Francis, Pleasantville, N.Y.

[73] Assignee: Ciba-Geigy Corporation, Ardsley, N.Y.

[21] Appl. No.: 219,808

[22] Filed: Dec. 24, 1980

Related U.S. Application Data

[63] Continuation of Ser. No. 74,441, Sep. 10, 1979, abandoned, which is a continuation-in-part of Ser. No. 882,004, Feb. 28, 1978, abandoned, which is a continuation-in-part of Ser. No. 790,508, Apr. 25, 1977, abandoned, which is a continuation-in-part of Ser. No. 699,016, Jun. 23, 1976, abandoned, which is a continuation-in-part of Ser. No. 590,221, Jun. 30, 1975, abandoned, which is a continuation-in-part of Ser. No. 494,948, Aug. 5, 1974, abandoned.

[51] Int. Cl.³ .................... A61K 31/135; C07C 87/28
[52] U.S. Cl. ........................... 424/330; 260/465 E; 562/441; 564/161; 564/165; 564/316
[58] Field of Search ................ 260/570 R, 570.8 R, 260/501.18; 424/316, 330; 564/355, 360, 316

[56] References Cited

U.S. PATENT DOCUMENTS

| | | | |
|---|---|---|---|
| Re. 23,100 | 4/1949 | Suter et al. | 260/570 R |
| 2,827,460 | 3/1958 | Stein et al. | 260/570 R |
| 3,073,842 | 1/1963 | Schlesinger et al. | 260/570 R |
| 3,152,173 | 10/1964 | Ehrhart et al. | 260/570.8 R |
| 3,847,950 | 11/1974 | Suh et al. | 260/570.8 R |
| 3,906,110 | 9/1975 | Francis | 564/316 |
| 3,936,450 | 2/1976 | Mauvernay et al. | 260/570 R |
| 4,220,663 | 9/1980 | Schulze et al. | 424/330 |

Primary Examiner—Ethel G. Love
Attorney, Agent, or Firm—Norbert Gruenfeld

[57] ABSTRACT 1-(Aralkoxyphenyl)-2 or 3-(bis-arylalkylamino)-alkanes, e.g. those of the formula:

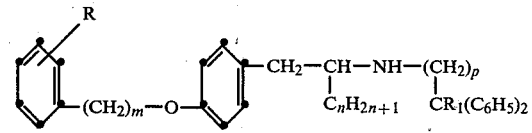

$R$ = H, alkyl, alkoxy, halogeno or $CF_3$
$R_1$ = H or OH
m, n, p = 1 or 2 or therapeutically acceptable salts thereof are hypotensive and cardioactive agents.

6 Claims, No Drawings

1-(ARALKOXYPHENYL)-2-(BIS-ARYLALKYLAMINO)-ALKANES

CROSS-REFERENCES TO RELATED APPLICATIONS

This is a continuation of application Ser. No. 074,441 filed on Sept. 10, 1979, now abandoned, which in turn is a continuation-in-part of application Ser. No. 882,004, filed Feb. 28, 1978, (now abandoned), which is a continuation-in-part of application Ser. No. 790,508, filed Apr. 25, 1977, (now abandoned), which is a continuation-in-part of application Ser. No. 699,016, filed June 23, 1976 (now abandoned), which is a continuation-in-part application Ser. No. 590,221, filed June 30, 1975, (now abandoned), which is a continuation-in-part of application Ser. No. 494,948 filed Aug. 5, 1974, (now abandoned).

SUMMARY OF THE INVENTION

The present invention concerns and has for its object the provision of new 1-(aralkoxyphenyl)-2 or 3-(bis-arylalkylamino)-alkanes, more particularly of those corresponding to Formula I

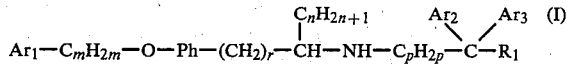

wherein each of $Ar_1$, $Ar_2$ and $Ar_3$ is unsubstituted phenyl or phenyl substituted by one or more than one member of lower alkyl, lower alkoxy, halogeno, trifluoromethyl, nitro, amino, mono- or di-lower alkylamino, lower alkanoylamino, cyano, carboxy, carbo-lower alkoxy carbamoyl, aminomethyl, mono- or di-lower alkylaminomethyl, Ph is unsubstituted phenylene, or phenylene substituted by one member listed for $Ar_1$, n is an integer from 0 to 4, each of m and p is an integer from 1 to 4, r is the integer 1 or 2 and $R_1$ is hydrogen or hydroxy, or of therapeutically useful salts thereof, as well as of corresponding pharmaceutical compositions and of methods for the preparation and application of said products, which are useful hypotensive and cardioactive agents.

DESCRIPTION OF THE PREFERRED EMBODIMENTS

Of the phenyl radicals $Ar_1$ is preferably phenyl substituted by up to five, advantageously one or two members of the group consisting of lower alkyl, e.g. methyl, ethyl, n- or i-propyl or -butyl; lower alkoxy, e.g. methoxy, ethoxy, n- or i-propoxy or -butoxy; halogeno, e.g. fluoro, chloro or bromo; trifluoromethyl; nitro; amino; mono- or di-lower alkylamino, e.g. mono- or dimethylamino, mono- or diethylamino; lower alkanoylamino, e.g. acetylamino, propionylamino or pivaloylamino; cyano; carboxy; carbo- lower alkoxy, e.g. carbomethoxy or carbethoxy; carbamoyl; aminomethyl; mono- or di-lower alkylaminomethyl, e.g. mono- or dimethylaminomethyl. Each of $Ar_2$ and $Ar_3$ is preferably unsubstituted phenyl, or phenyl substituted by one member of the group listed for $Ar_1$. The term "lower," referred to above or hereinafter in connection with organic radicals or compounds respectively, defines such with up to 4, preferably up to 3, advantageously such with one or two carbon atoms.

The phenylene radical Ph is preferably unsubstituted 1,4-phenylene, but also 1,2- or 1,3-phenylene, or such phenylene substituted by one member of lower alkyl, lower alkoxy, halogeno or trifluoromethyl, e.g. those listed for $Ar_1$; and $R_1$ is preferably hydrogen, but also hydroxy.

The lower alkyl group $C_nH_{2n+1}$ preferably represents methyl, but also any other member mentioned above. The lower alkylene group $C_mH_{2m}$ preferably stands for $(CH_2)_m$, especially methylene, but also for 1,1- or 1,2-ethylene, 1,1-, 2,2-, 1,2- or 1,3-propylene or -butylene; and $C_pH_{2p}$ preferably represents $(CH_2)_p$, especially 1,2-ethylene, but also any other of said alkylene groups.

Salts of the compounds of Formula I are preferably therapeutically acceptable acid addition salts, e.g. those derived from the acids listed below.

The compounds of the invention exhibit valuable pharmacological properties, primarily hypotensive, antihypertensive and bradycardic activity. This is demonstrable in animal tests, using advantageously mammals, e.g. rats, cats or monkeys, as test objects. The animals may either be normotensive or hypertensive, e.g. genetically or adrenal regeneration hypertensive rats. Said compounds can be applied to them enterally or parenterally, advantageously orally, or subcutaneously, intraveneously, intraperitoneally or intraduodenally, for example within gelatin capsules or in the form of starchy suspensions or aqueous solutions respectively. The applied dosage may range between about 0.1 and 100 mg/kg/day, preferably between about 1 and 50 mg/kg/day, advantageously between about 5 and 25 mg/kg/day. The lowering effect on the blood pressure is recorded either directly by means of a catheter, for example placed in the rat's caudal artery, or indirectly by sphygmomanometry at the rat's tail, and a transducer, expressing the blood pressure prior and after dosing in mm Hg. Thus, for example, the d,l-1-[4-(3-trifluoromethylbenzyloxy)-phenyl]-2-(3,3-diphenyl-propylamino)-propane, a representative member of the compounds of the invention, advantageously in the form of its hydrochloride, or preferably the levorotatory antipode thereof, are very effective in said hypertensive rats at p.o. doses as low or lower than 5 mg/kg/day and maximally about 24 hours after dosing. Antihypertensive doses cause only minor impairment of sympathetic nerve function, unlike antihypertensive agents which act by adrenergic neuron blockade, as assessed by pressor responses to electrical stimulation of the spinal cord of pithed rats. Said member also differs from certain centrally acting antihypertensive agents cause cause sedation. Moreover, said l-hydrochloride does not cause brain norepinephrine-depletion, unlike other centrally acting agents, although it does cause depletion in peripheral tissues, such as the heart. Furthermore, it does not produce sedation in monkeys at hypotensive dose, as does α-methyldopa. Accordingly, the compounds of the invention are useful antihypertensive and bradycardic agents, for example in the treatment of management of primary or secondary hypertension, or angina pectoris respectively. They are also useful intermediates in the preparation of other valuable products, especially of pharmacologically active compositions.

Particularly useful for said purpose are compounds of Formula I, in which each of $Ar_1$, $Ar_2$ and $Ar_3$ is phenyl, (lower alkyl)$_q$-phenyl, (lower alkoxy)$_q$-phenyl, (halogeno)$_q$-phenyl or (trifluoromethyl)-phenyl, Ph is 1,3- or 1,4-phenylene, (lower alkyl)-1,3- or 1,4-phenylene, (lower alkoxy)-1,3- or 1,4-phenylene, (halogeno)-1,3- or 1,4-phenylene or (trifluoromethyl)-1,3- or 1,4-phenylene, n is an integer from 1 to 4, each of m and p is an integer from 1 to 4, q is an integer from 1 to 5, r is the integer 1 or 2 and $R_1$ is hydrogen or hydroxy, or a therapeutically useful acid addition salts thereof.

Outstanding compounds of the invention due to their high degree of activity are those of Formula II

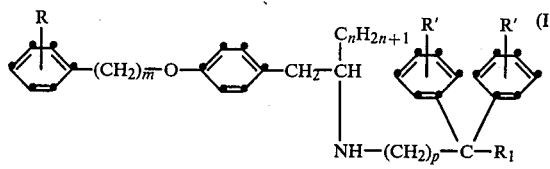

wherein each of R and R' is hydrogen, alkyl or alkoxy with up to 4 carbon atoms, fluoro, chloro, bromo or trifluoromethyl, each of m, n and p is the integer 1 or 2, and $R_1$ is hydrogen or hydroxy, or therapeutically acceptable acid addition salts thereof.

More preferred are those compounds of Formula II, wherein $R_1$, m, n and p have the meaning given in the preceding paragraph, R is methyl, methoxy, chloro or trifluoromethyl and R' is hydrogen, or therapeutically acceptable acid addition salts thereof.

Most preferred are the compounds of Formula II, wherein R is meta- or para-(chloro or trifluoromethyl), $R_1$ and R' are hydrogen, each of m and n is the integer 1 and p the integer 2, or therapeutically acceptable acid addition salts thereof.

The compounds of the invention are prepared according to methods known per se, advantageously by:

(1) reducing carbonyl compounds of Formula III

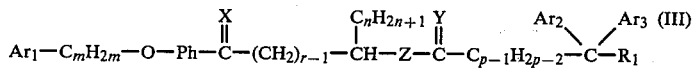

wherein one or both of X and Y is oxygen and the other is $H_2$ and Z is free or protected NH.

A protected amino group Z is preferably such, that can easily be liberated, e.g. by hydrolysis or hydrogenolysis, for example, an amide or advantageously benzylic grouping, such as a lower alkanoyl-, aralkanoyl- or α-aralkylamino group, e.g. $C_nH_{2n+1}$—CON or $Ar_1$—$C_nH_{2n}$—CON when $Y=H_2$, or $C_nH_{2n+1}$—CHAr$_1$—N when $Y=O$ or $H_2$.

The reduction of the ketones and/or amides III is performed according to known methods, the former, for example, by the reaction of the Ketone with an arylsulphonylhydrazide followed by treatment with sodium borohydride. Amides are advantageously reduced with the use of reducing agents, such as simple or complex light metal hydrides, such as boranes or aluminum hydride, preferably alkali metal boron or aluminum hydrides, e.g. lithium aluminum hydride, sodium borohydride or lithium or sodium tri-lower alkoxy- or bisalkoxyalkoxyaluminum hydrides, such as lithium tri-t.butoxy- or sodium bis-(2-methoxy-ethoxy)-aluminum hydride.

The starting material can be prepared according to methods known per se, e.g. those illustrated by the examples herein. Thus, for example, the products III are obtained from the corresponding phenolates, such as alkali metal, e.g. sodium or potassium salts, of the phenols HO—Ph—CX—$(CH_2)_{r-1}$—CH$(C_nH_{2n+1})$—Z—CY—$C_{p-1}H_{2p-2}$—CH($Ar_2$, $Ar_3$) and reactive esters of the alcohols $Ar_1$—$C_mH_{2m}$—CH, e.g. such derived from a strong inorganic or organic acid, preferably a hydrohalic, e.g. hydrochloric, -bromic or -iodic acid, or an alkane or benzene sulfonic acid, e.g. methane, p-toluene or m-bromobenzene sulfonic acid. Also amines $Ar_1$—$C_mH_{2m}$—C—Ph—CX—$(CH_2)_{r-1}$ CH—$(C_nH_{2n+1})$—ZH can be reacted with reactive, functional derivatives of the acids HOOC—$C_{p-1}H_{2p-2}$C—$R_1(Ar_2Ar_3)$, e.g. halides or anhydrides thereof. The former phenols are either known or can be obtained by condensing compounds disclosed in Belgian Pat. No. 660,217, e.g. those of formula HO—Ph—CO—CHNH$_2$—$C_nH_{2n+1}$, with said alcohol or acid derivatives respectively, in subsequent steps and also according to the conditions mentioned under item (3) below.

Another method for preparing the compounds of Formula I consists in:

(2) reducing olefins or Schiff's bases of Formula IV

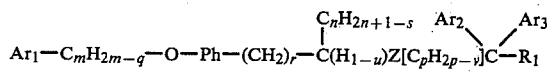

wherein one of q, s and v is the integer 2 and the others 0 or 2, u is 0, and Z is free or protected NH or Z is N, either u is 1 or v is 1 or 3 and the other integers have the meaning given above.

For materials in which $R_1$ is hydrogen, the desired compounds are prepared by reducing olefins or Schiff's bases of Formula IVa

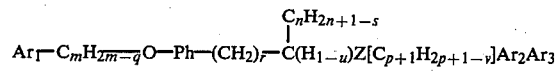

wherein one of q, s and v is the integer 2 and the others 0 or 2, u is 0 and Z is free or protected NH, or Z is N, either u is 1 or v is 1 or 3 and the other integers have the meaning given above.

The reduction of compounds IV and IVa is carried out according to known methods, for example with the use of hydrogen in the presence of catalysts, e.g. platinum or nickel catalysts, or with nascent hydrogen, e.g. generated electrolytically, which is advantageously applied to the Schiff's bases IV and IVa. They can also be reduced with the reducing agents mentioned under item 1, preferably with simple light metal hydrides, e.g. boranes. Schiff's bases with n=0, u or v=1(or 3) respectively, can also be reduced with $C_nH_{2n+1}$-Grignard compounds, e.g. lower alkyl-magnesium halides, and the metal adducts hydrolysed with water or aqueous ammonium salts, in order to obtain compounds of Formula I with n=1 to 4 or branched $C_pH_{2p}$.

The olefins IV and IVa are obtained analogously to the carbonyl compounds III, by choosing the above condensations with the corresponding unsaturated compounds, i.e. reactive esters of the alcohol $Ar_1$—$C_mH_{2m-q}$—OH, or derivatives of the acid HOOC[$C_{p-1}H_{2p-2-v}$]CR$_1$Ar$_2$Ar$_3$ for preparing IV or derivatives of the acid HOCC[$C_pH_{2p-1-v}$]Ar$_2$Ar$_3$ for preparing Iva and reducing in any resulting amide the carbonyl group with said reducing agents mentioned under item (1), preferably with complex light metal hydrides, e.g. lithium aluminum hydride. The Schiff's bases IV are obtained from the corresponding free or protected amines HO—Ph—(CH$_2$)$_r$—CHN-H$_2$—C$_n$H$_{2n+1-s}$ by condensation with the aldehyde OHC—[C$_{p-1}$H$_{2p-2-v}$]CR$_1$Ar$_2$Ar$_3$, followed by a reactive ester of Ar$_1$C$_m$H$_{2m-q}$OH.

Schiff's bases IV are also obtained from the corresponding free or protected ketones HO—Ph—(CH$_2$)$_r$—CO—C$_n$H$_{2n+1-s}$ by condensation with an amine H$_2$N[C$_p$H$_{2p-v}$]CR$_1$Ar$_2$Ar$_3$, followed by a reactive ester of Ar$_1$—C$_m$H$_{2m-q}$OH.

The Schiff's bases IVa are obtained from the free or protected amines HO—Ph—(CH$_2$)$_r$—CHN-H$_2$—C$_n$H$_{2n+1-s}$ by condensation with the aldehyde OHC—[C$_p$H$_{2p-1-v}$]Ar$_2$Ar$_3$, followed by a reactive ester of Ar$_1$—C$_m$H$_{2m-r}$—OH. Schiff's bases IVa are also obtained from the corresponding free or protected ketones HO—Ph—(CH$_2$)$_r$—CO—C$_n$ H$_{2n+1-s}$ by condensation with an amine H$_2$N—[C$_{p+1}$H$_{2p+1-v}$]Ar$_2$Ar$_3$, followed by a reactive ester of Ar$_1$—C$_m$H$_{2m-q}$—OH.

Another method for preparing the compounds of Formula I consists in:

(3) condensing compounds of Formula V and VI
(V) Ar$_1$—C$_m$H$_{2m}$—T + U—C$_p$H$_{2p}$—CR$_1$Ar$_2$Ar$_3$
(VI)

or reactive salts thereof, wherein one of T and U is the group (O—Ph—(CH$_2$)$_r$—CH(C$_n$H$_{2n+1}$)Z")H in which Z" is free or protected NH, and the other of T and U is reactively esterified OH, or U is amino and T said moiety wherein Z" is reactively esterified OH, e.g. bromo.

The condensation of V and VI is preferably carried out with the use of reactive salts of the phenols or amines respectively, such as alkali metal, e.g. sodium or potassium salts, or in the presence of condensing agents, neutralizing the eliminated acids (TH, UH or Z"H) and/or attracting any water formed, such as inorganic or organic (nitrogen) bases, e.g. alkali or alkaline earth metal carbonates or hydrogencarbonates; tri-lower alkylamines or pyridines, or anhydrous forms of salt hydrates or azeotropic solvents respectively.

The compounds V and VI are similarly prepared as the above starting material, e.g. from HO—Ph—(CH$_2$)$_r$—CH(C$_n$H$_{2n+1}$)Z" by condensation with Ar$_1$—C$_m$H$_{2m}$—T or U—C$_p$H$_{2p}$—CH(Ar$_2$Ar$_3$), wherein T is reactively esterified OH and one of U and Z" is T and the other NH$_2$. The protection of the amino groups can be carried out in the usual manner, e.g. similar to the procedures shown in French Pat. Nos. 2,013,686 and 2,013,689.

Either in the course of the above reactions 1 to 3, or subsequently, any protected or metallized amino group Z and Z" can be liberated in the usual manner, e.g. by hydrolysis of the amide groupings, or by hydrogenolysis of the α-aralkyl groups, e.g. either with the use of water alone or preferably aqueous acids or bases respectively, advantageously aqueous mineral acids or alkali metal hydroxides or catalytically activated hydrogen.

The resulting compounds of the invention can be converted into each other according to known methods. Thus, for example, any resulting halogen compound can be dehalogenated either in the course of any of the above hydrogenations or subsequently under more drastic conditions, e.g. higher temperature and/or pressure, and the course of these reactions is easily observed and controlled by the amount of consumed hydrogen. Moreover, the compounds of the invention are obtained in the free form or in the form of their acid addition salts, depending on the conditions under which the process is carried out. Salts that are obtained can be converted into the free bases in known manner, for example, with ammonia, alkalies or ion exchangers. Free bases that are obtained can be converted into salts by neutralization with acids, especially those that are suitable for the formation of therapeutically useful acid addition salts. Such acids are inorganic or organic acids, for example, mineral acids, such as a hydrohalic, e.g. hydrochloric or hydrobromic acid; sulfuric, phosphoric, nitric or perchloric acid: aliphatic or aromatic carboxylic or sulfonic acids, such as formic, acetic, propionic, succinic, glycollic, lactic, malic, tartaric, citric, ascorbic, maleic, hydroxymaleic, pyruvic, phenylacetic, benzoic, aminobenzoic, anthranilic, 4-hydroxybenzoic, salicylic, 4-aminosalicylic, embonic, nicotinic, methanesulfonic, ethanesulfonic, hydroxyethanesulfonic, ethylenesulfonic, halobenzenesulfonic, toluenesulfonic, naphthalenesulfonic, sulfanilic or cyclohexylsulfamic acid; methionine, tryptophan, lysine or arginine. These or other salts, for example, the picrates, can also be used in the purification of the free compounds. In view of the close relationship between the salts and the free compounds, whenever such is referred to in this context, a corresponding salt is also intended, provided such is possible or appropriate under the circumstances.

Resulting mixtures of isomers can be separated into the single isomers by methods in themselves known, e.g. by fractional distillation, crystallization and/or chromatography. Racemic products can likewise be resolved into the optical antipodes, for example, by separation of diastereomeric salts thereof, e.g. by the fractional crystallization of d- or l-tartrates.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g. those of Formula II and especially the levorotatory antipodes thereof.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweetners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods respectively, and contain about 0.1 to 75%, preferably about 1 to 50%, of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

The mixture of 210 g of 1-[4-(3-chlorobenzyloxy)-phenyl]-2-aminopropane, 158 g of β-phenylcinnamaldehyde and 1 lt. of dry benzene is stirred at reflux in an apparatus containing a water trap until no more water is collected. The solution is evaporated, the residue triturated in 1 lt of dry tetrahydrofuran and added dropwise under nitrogen to the cooled, stirring slurry of 86.5 g of lithium aluminum hydride in 1.5 lt of dry tetrahydrofuran. The whole is stirred at ambient temperature for 20 hours, then cooled and treated cautiously with saturated aqueous ammonium chloride until the remaining hydride has been destroyed. The mixture is filtered. The residue is washed with chloroform & the chloroform filtrate washed with water, dried and evaporated. The residue is dissolved in acetone & the solution treated with ethereal hydrogen chloride until acidic. On cooling and adding dry diethyl ether little by little, the 1-[4-(3-chlorobenzyloxy)-phenyl]-2-(3,3-diphenyl-propylamino)-propane hydrochloride is obtained, melting at 157°–160° after recrystallization from methanol-diethyl ether.

The starting material is prepared as follows: To the stirring mixture of 244 g of p-hydroxybenzaldehyde, 360 g of potassium carbonate, 32 g of potassium iodide, 1.2 lt of 95% aqueous ethanol and 160 ml of water is added slowly 367 g of m-chlorobenzyl chloride. The mixture is stirred at reflux for four hours, cooled to 80° and 2 lt of warm water are added while stirring. The mixture is cooled, the precipitate collected, washed with water and recrystallized from methanol, to afford the 4-(3-chlorobenzyloxy)-benzaldehyde melting at 51°–54°.

The mixture of 200 g thereof, 40 g of ammonium acetate and 400 ml of nitroethane is heated under reflux for forty minutes and allowed to cool. The precipitate is filtered, pressed dry and recrystallized from ethanol, to yield the 1-[4-(3-chlorobenzyloxy)-phenyl]-2-nitropropene melting at 117°–118°. The solution of 91 g thereof in 600 ml of tetrahydrofuran is added dropwise to the cooled slurry of 57 g of lithium aluminum hydride in 750 ml of dry tetrahydrofuran while stirring under nitrogen. The mixture is stirred at ambient temperature for 18 hours and then cautiously treated dropwise with saturated aqueous ammonium chloride while cooling, until the remaining hydride is destroyed. It is filtered, the precipitate washed with chloroform, the filtrate washed with water, dried and evaporated, to afford the 1-[4-(3-chlorobenzyloxy)-phenyl]-2-aminopropane as an oil; the hydrochloride thereof melts at 152°–154°.

EXAMPLE 2

Analogously the d,l-1-[4-(4-chlorobenzyloxy)-phenyl]-2-(3,3-diphenylpropylamino)-propane hydrochloride, m.p. 178°–180°, is prepared from the 4-(4-chlorobenzyloxy)-benzaldehyde, m.p. 73°–75°, 1-[4-(4-chlorobenzyloxy)-phenyl]-2-nitropropene, m.p. 99°–100° C., and 1-[4-(4-chlorobenzyloxy)-phenyl]-2-aminopropane, the hydrochloride of the latter melts at 199°–201.5°.

EXAMPLE 3

To the solution of 85 g of 1-(4-hydroxyphenyl)-2-(3,3-diphenylpropylamino)-propane hydrochloride (m.p. 204°–207° C., prepared from the free base which, in turn, is prepared as described by Ehrhart et al, U.S. Pat. No. 3,152,173) in 50 ml of dimethylsulfoxide is added 4.1 ml of 10 N aqueous sodium hydroxide and the whole is brought to 60° and maintained at this temperature for one hour. To this are added 4.0 g of 3,4-dichlorobenzyl chloride and the whole is stirred vigorously at ambient temperature for 20 hours. The mixture is poured into 500 ml of ice-water containing 5 ml of 10 N aqueous sodium hydroxide and extracted with ethyl acetate. The extract is washed with saturated aqueous sodium chloride, dried and evaporated. The residue is dissolved in the minimum amount of isopropanol, the solution treated with ethereal hydrogen chloride to acidity and refrigerated whereupon the 1-[4-(3,4-dichlorobenzyloxy)-phenyl]-2-(3,3-diphenylpropylamino)-propane hydrochloride separates melting at 147°–148°.

EXAMPLE 4

When p-cyanobenzyl chloride is substituted for 3,4-dichlorobenzyl chloride of Example 3, the 1-[4-(4-cyanobenzyloxy)-phenyl]-2-(3,3-diphenylpropylamino)-propane is obtained. Extraction of the aqueous mixture with ethyl acetate yields the free base melting at 132° to 138.5°.

EXAMPLE 5

The mixture of 11.9 g of 4-(4-chlorobenzyloxy)-phenylacetone, 9.8 g of 3,3-diphenyl-3-hydroxypropylamine and 100 ml of absolute ethanol is heated under reflux for one hour, cooled to room temperature and treated little by little under stirring with 6 g of sodium borohydride in 25 ml of water. The mixture is stirred for 18 hours, poured into ice-water, the resulting precipitate collected, washed with water and recrystallized from isopropanol. It is taken up in chloroform, the solution treated with charcoal, filtered, evaporated and the residue recrystallized from isopropanol to afford the d,l-1-[4-(4-chlorobenzyloxy)-phenyl]-2-(3,3-diphenyl-3-hydroxypropylamino)-propane melting at 125° to 127°.

The starting material is prepared as follows: The mixture of 30.4 g of 1-[4-(4-chlorobenzyloxy)-phenyl]-2-nitropropene (Example 2), 80 g of iron powder, 3.2 g of ferric chloride, 40 ml of concentrated hydrochloride acid, 400 ml of ethanol and 1.2 lt of water is stirred vigorously at refux for ten hours, cooled and filtered.

The residue is washed with methanol, the filtrate evaporated and the residue dissolved in hot isopropanol. The solution is treated with charcoal, filtered, the filtrate refrigerated, the precipitate collected, washed with petroleum ether and dried, to afford the 4-(4-chlorobenzyloxy)-phenylacetone melting at 76°–80°.

EXAMPLE 6

The mixture of 16.0 g of 1-1-(4-hydroxyphenyl)-2-(3,3-diphenylpropylamino)-propane hydrochloride, 50 ml of dimethylsulfoxide and 3.4 g of sodium hydroxide in 10 ml water is stirred at 60° for 1 hour, whereupon 7.2 g of 4-chlorobenzyl chloride are added and the whole is stirred over night at room temperature. The mixture is poured into 300 ml of N-aqueous sodium hydroxide, extracted with methylene chloride & the extract dried and evaporated. The residue is dissolved in 250 ml of ethyl acetate, the solution combined with that of 7.0 g of maleic acid in 25 ml of methanol & the mixture stirred for 1 hour and filtered, to yield the 1-1-[4-(4-chlorobenzyloxy)-phenyl]-2-(3,3-diphenylpropylamino)-propane maleate melting at 177°–178°, $[M]_D = 58.1°$ (5% in methanol).

The starting material is prepared as follows: The mixture of 23 g of 1-1-(4-hydroxyphenyl)-2-aminopropane, 31.2 g of 3,3-diphenylacrolein, 150 ml of anhydrous ethanol and 4 g of 10% palladium on charcoal is hydrogenated at 3.3 atm. for 6 hours. It is filtered, the filtrate evaporated, the residue dissolved in 400 ml of isopropanol and the solution combined with 12.5 ml of concentrated hydrochloric acid. After standing overnight the precipitate is collected and washed with isopropanol and diethyl ether, to yield the 1-1-(4-hydroxyphenyl)-2-(3,3-diphenylpropylamino)-propane hydrochloride melting at 244°–247°; $[M]HD \, D = 35.1°$ (5% in methanol).

Analogously its dextrorotatory antipode is obtained, melting at 244°–246°; $[M]_D = +31.9°$ (5% in methanol), which is converted as shown above into the d-1-[4-chlorobenzyloxy)-phenyl]-2-(3,3-diphenylpropylamino)-propane maleate melting at 176°–178°, $[M]_D = +57.3°$ (5% in methanol).

EXAMPLE 7

The mixture of 11.85 g of 1-(4-hydroxyphenyl)-3-(3,3-diphenylpropylamino)-butane (U.S. Pat. No. 3,262,977), 50 ml of dimethylsulfoxide and 3.1 ml of 10 N-aqueous sodium hydroxide is stirred at 80° for ½ hour, whereupon 5.1 g of 4-chlorobenzyl chloride are added and the whole is stirred for 8 hours while allowing to cool to room temperature. The mixture is poured into 600 ml of ice-cold N-aqueous sodium hydroxide, extracted with a total of 700 ml of ethyl acetate, the extract washed with saturated aqueous sodium chloride, dried and evaporated. The residue is taken up in the minimum amount of anhydrous ethanol, the solution combined with that of 3.48 g of maleic acid in ethanol, cooled and the precipitate collected, to yield the 1-[4-(4-chlorobenzyloxy)-phenyl]-3-(3,3-diphenylpropylamino)-butane maleate melting at 154°–156°.

EXAMPLE 8

The mixture of 17.3 g of 1-(3-hydroxyphenyl)-2-(3,3-diphenylpropylamino)-propane, 100 ml of dimethylsulfoxide and 5 ml of 10 N-aqueous sodium hydroxide is stirred at room temperature for ½ hour, combined with 8.05 g of 4-chlorobenzyl chloride and stirred 16 hours longer. It is poured into water, extracted with ethyl acetate, the extract washed with saturated aqueous sodium chloride, dried and evaporated. The residue is taken up in diethyl ether, the solution acidified with isopropanolic hydrogen chloride, the precipitate collected and washed with diethyl ether, to yield the 1-[3-(4-chlorobenzyloxy)-phenyl]-2-(3,3-diphenylpropylamino)-propane hydrochloride melting at 184°–189°.

Analogously the 1-[3-(2-chlorobenzyloxy)-phenyl]-2-(3,3-diphenylpropylamino)-propane hydrochloride is prepared melting at 165°–167°; as well as the 1-[2-(3-chlorobenzyloxy)-phenyl]-2-(3,3-diphenylpropylamino)-propane hydrochloride, melting at 144°–145°.

The starting material is prepared as follows: The mixture of 100 g of m-methoxyphenylacetone, 129 g of 3,3-diphenylpropylamine and 500 ml of anhydrous ethanol is refluxed for 2 hours, cooled to 20° and the solution of 95 g of sodium borohydride in 300 ml of water is added dropwise while stirring at room temperature. After stirring overnight the mixture is poured into water, extracted with methylene chloride, the extract dried and evaporated. The residue is taken up in diethyl ether, the solution acidified with isopropanolic hydrogen chloride and the precipitate collected, to yield the 1-(3-methoxyphenyl)-2-(3,3-diphenylpropylamino)-propane hydrochloride melting at 95°–98°.

The mixture of 145 g thereof and 1.5 lt of 48% hydrobromic acid is refluxed for 45 minutes and allowed to stand at room temperature overnight. It is poured onto 4 kg of ice and 1 lt of concentrated ammonium hydroxide, the mixture extracted with methylene chloride, the extract dried, evaporated and the residue recrystallized from ethyl acetate, to yield the 1-(3-hydroxyphenyl)-2-(3,3-diphenylpropylamino)-propane melting at 122°–124°.

Reacting the (3-methoxy-4-hydroxyphenyl)-acetone with the 3,3-diphenylpropylamine, reducing the resulting Schiff's base as shown above and reacting the resulting saturated compound with 3-trifluoromethylbenzyl chloride, the 1-[3-methoxy-4-(3-trifluoromethylbenzyloxy)-phenyl]-2-(3,3-diphenylpropylamino)-propane hydrochloride is obtained, melting at 142° to 146° after recrystallization from isopropanol.

EXAMPLE 9

The mixture of 7.18 g of 1-(3-methyl-4-hydroxyphenyl)-2-(3,3-diphenylpropylamino)-propane, 50 ml of dimethylsulfoxide and 2 ml of 10 N-aqueous sodium hydroxide is stirred for 1 hour at 60°. After cooling to room temperature 3.32 g of 4-chlorobenzyl chloride are added and the mixture stirred overnight at said temperature. It is poured into water, extracted with ethyl acetate, the extract dried and evaporated. The residue is taken up in isopropanol, the solution acidified with isopropanolic hydrogen chloride, the precipitate collected and washed with diethyl ether, to yield the 1-[3-methyl-4-(4-chlorobenzyloxy)-phenyl]-2-(3,3-diphenylpropylamino)-propane hydrochloride melting at 166°–168°.

Analogously the 1-[3-fluoro-4-(4-chlorobenzyloxy)-phenyl]-2-(3,3-diphenylpropylamino)-propane hydrochloride is obtained, melting at 183°–187°.

The starting material is prepared as follows: The mixture of 100 g of 3-methyl-4-methoxybenzaldehyde, 300 ml of nitroethane and 52 g of ammonium acetate is refluxed for 4 hours and evaporated, to yield the 1-(3-methyl-4-methoxyphenyl)-2-nitropropene.

The solution of 185.9 g thereof in 500 ml of tetrahydrofuran is added dropwise to the slurry of 76 g of lithium aluminum hydride in 250 ml of tetrahydrofuran while stirring and cooling with ice-sodium chloride and stirring is continued overnight at room temperature under nitrogen. The mixture is slowly combined with 300 ml of saturated aqueous ammonium chloride & diluted with 2 lt of diethyl ether to facilitate stirring and filtered. The residue is washed with a total of 1.5 lt of diethyl ether & the filtrate washed with saturated aqueous sodium chloride, dried and evaporated. The residue is taken up in diethyl ether, the solution acidified with ethanolic hydrogen chloride and the precipitate collected, to yield the 1-(3-methyl-4-methoxyphenyl)-2-aminopropane hydrochloride melting at 200°-205°.

19.7 g thereof are added to the solution of 4.93 g of sodium methoxide in 300 ml of anhydrous ethanol while stirring. After a few minutes the mixture is filtered, the filtrate evaporated and the residue taken up in 500 ml of benzene. The solution is combined with 19.01 g of 3,3-diphenylacrolein, refluxed for $2\frac{1}{2}$ hours on a water trap and evaporated. The residue is taken up in 250 ml of tetrahydrofuran, the resulting solution combined with 14 g of lithium aluminum hydride and the mixture refluxed for 60 hours while stirring under nitrogen. It is combined with 250 ml of saturated aqueous ammonium chloride, filtered & the residue washed with diethyl ether & ethyl acetate. The organic extract is washed with saturated aqueous sodium chloride, dried & evaporated. The residue is taken up in diethyl ether, the solution neutralized with ethanolic hydrogen chloride and the precipitate recrystallized from isopropanol, to yield the 1-(3-methyl-4-methoxyphenyl)-2-(3,3-diphenylpropylamino)-propane hydrochloride melting at 174°-179°.

The mixture of 20.5 g thereof, 100 ml of methylene chloride and 50 g of boron tribromide is stirred at 0° for 9 hours and at room temperature for 9 hours. It is evaporated, the residue poured onto ice and saturated ammonium hydroxide, the mixture filtered and the precipitate recrystallized from benzene, to yield the 1-(3-methyl-4-hydroxyphenyl)-2-(3,3-diphenylpropylamino)-propane melting at 115°-118°.

The similarly prepared 3-fluoro-analog melts at 186°-188° after recrystallization from methyl cellosolve.

EXAMPLE 10

According to the methods illustrated by the previous examples, preferably according to those mentioned under item (3) herein, the following racemic products of Formula I are prepared from equivalent amounts of the corresponding starting materials: m=n=r=1, p=2, Ph=1,4-phenylene, $Ar_2=Ar_3$=phenyl, $R_1=H$

| No. | $Ar_1$ | Salt | m.p. ° C. |
|---|---|---|---|
| 1 | 4-F-phenyl | maleate | 161–163 |
| 2 | $F_5$-phenyl | " | 156–158 |
| 3 | 4-Cl-phenyl | " | 183–184 |
| 4 | 4-Br-phenyl | " | 183–185 |
| 5 | 3-$CF_3$-phenyl | " | 135–137 |
| 6 | 4-NC-phenyl | " | 80–82 |
| 7 | 4-$H_2$NCO-phenyl | " | 184–185 |
| 8 | 3-$H_2$NCO-phenyl | hemifumarate | 188–190 |

EXAMPLE 11

The mixture of 4.8 g of 1-[4-(4-carbamoylbenzyloxy)-phenyl]-2-(3,3-diphenylpropylamino)-propane (prepared from the maleate of Example 10/8 by extracting the suspension thereof in 100 ml of N-aqueous sodium hydroxide with methylene chloride and evaporating the dried extract), 25 ml of ethanol, 10 ml of water and 5.6 g of potassium hydroxide is refluxed for 18 hours under nitrogen. It is concentrated, the concentrate diluted with 75 ml of water and acidified with 10 ml of concentrated hydrochloric acid. The precipitate is filtered, washed with water, dried and triturated with diethyl ether, to yield the 1-[4-(4-carboxybenzyloxy)-phenyl]-2-(3,3-diphenylpropylamino)-propane hydrochloride melting at 188°-190°.

EXAMPLE 12

Preparation of 10,000 tablets each containing 50.0 mg of the active ingredient:

| Formula: | |
|---|---|
| p-1-[4-(4-chlorobenzyloxy)-phenyl]-2-(3,3-diphenylpropylamino)-propane maleate | 500.00 g |
| Lactose | 1,706.00 g |
| Corn starch | 90.00 g |
| Polyethylene glycol 6,000 | 90.00 g |
| Talcum powder | 90.00 g |
| Magnesium stearate | 24.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

Preparation of 10,000 capsules each containing 100 mg of the active ingredient:

| Formula: | |
|---|---|
| d,p-1-[4-(4-chlorobenzyloxy)-phenyl]-2-(3,3-diphenylpropylamino)-propane hydrochloride | 1,000.0 g |
| Lactose | 2,800.0 g |
| Talcum powder | 200.0 g |

Procedure:

All the powders are passed through a screen with openings of 0.6 mm. Then the drug substance is placed in a suitable mixer and mixed first with the talcum, then with the lactose until homogenous. No. 1 capsules are filled with 400 mg each, using a filling machine.

Analogously tablets and capsules are prepared from the remaining compounds illustrated by the other examples.

EXAMPLE 13

According to the method illustated by Example 6 herein, the following compounds are prepared:

(1a)   1-1-[4-(4-carbamoylbenzyloxy)-phenyl]-2-(3,3-diphenylpropylamino)-propane maleate, m.p. 178°-180°, $[M]_D = -47.6°$; and (b) its antipode m.p. 171°-173°, $[M]_D = +41.0°$;

(2) l-1-[4-(3-trifluoromethylbenzyloxy)-phenyl]-2-(3,3-diphenylpropylamino)-propane hydrochloride, m.p. 151°–152°, $[M]_D = -42.1°$;

(3a) l-1-[4-(4-trifluoromethylbenzyloxy)-phenyl]-2-(3,3-diphenylpropylamino)-propane hydrochloride, m.p. 131–133, $[M]_D = -40.0°$ or (b) its maleate m.p. 165°–167° $[M]_D = -49.6°$;

(4) l-1-(4-benzyloxyphenyl)-2-(3,3-diphenylpropylamino)-propane hydrochloride, m.p. 174°–176°, $[M]_D = -46.7°$;

(5) l-1-[4-(3-methylbenzyloxy)-phenyl]-2-(3,3-diphenylpropylamino)-propane hydrochloride, m.p. 181°–183°, $[M]_D = -43.3°$. (all above rotations at c=1 in methanol).

EXAMPLE 14

To the suspension of 5.0 g of racemic 1-[4-(4-carbamoylbenzyloxy)-phenyl]-2-(3,3-diphenylpropylamino)-propane (Example 10/7) in 75 ml of tetrahydrofuran, 70 ml of 1-molar diborane in tetrahydrofuran are added dropwise while stirring under nitrogen at 0°. It is refluxed for 18 hours, cooled to 0° again and 30 ml of water are added dropwise, followed by 15 ml of concentrated hydrochloric acid. The mixture is evaporated, warmed with 50 ml of methanol, evaporated again and the residue is recrystallized from ethanol, to yield the 1-(4-(4-aminomethylbenzyloxy)-phenyl]-2-(3,3-diphenylpropylamino)-propane dihydrochloride melting at 259°–262°.

Its analogously obtained optically active form (of the amide of Example 13/1a) melts as dihydrochloride hemihydrate at 249°–252°, $[M]_D = -14.2°$ (c=1 in methanol).

EXAMPLE 15

The mixture of 10.0 g 1-(4-hydroxyphenyl)-2-(3,3-diphenylpropylamino)-propane, 50 ml of dimethylsulfoxide and 2.4 g of sodium hydroxide in 10 ml of water is stirred at 60° for a half hour, whereupon 5.9 g of 2-cyanobenzyl bromide are added and the whole is stirred at room temperature for 20 hours. The mixture is diluted with water, extracted with ethyl acetate & the extract dried and evaporated. The residue is dissolved in the minimum amount of isopropanol, the solution neutralized with isopropanolic oxalic acid and the crude precipitate chromatographed on silica gel, using chloroform eluate, followed by chloroform-methanol (1:1). The initial fraction yields the 1-[4-(2-cyanobenzyloxy)-phenyl]-2-(3,3-diphenylpropylamino)-propane, showing I. R. bands at 2220 and 907 cm$^{-1}$, and the second fraction the 1-[4-(2-carbamoylbenzyloxy)-phenyl]-2-(3,3-diphenylpropylamino)-propane, showing I. R. bands at 1655 and 1450 cm$^{-1}$. The latter amide is taken up in aqueous ammonia, the mixture extracted with ethyl acetate & the extract dried and acidified with ethereal hydrogen chloride, to yield the corresponding hydrochloride melting at about 100° with decomposition.

EXAMPLE 16

The mixture of 2.4 g of 1-[4-(4-carbamoylbenzyloxy)-phenyl]-2-(3,3-diphenylpropylamino)-propane, 3.6 g of boron trifluoride etherate and 20 ml of methanol is heated in a sealed tube at 115° for 6 hours. After cooling it is diluted with water, extracted with ethyl acetate, the extract dried, concentrated and the concentrate neutralized with maleic acid in ethyl acetate, to yield the 1-[4-(4-carbomethoxybenzyloxy)-phenyl]-2-(3,3-diphenylpropylamino)-propane maleate melting at 172°–175°.

EXAMPLE 17

To the suspension of 11.2 g of dl-1-(p-benzyloxyphenyl)-2-(3,3-diphenylpropionamido)-propane in 200 ml of tetrahydrofuran, 150 ml of 1 molar borane in tetrahydrofuran are added dropwise while stirring under nitrogen at 0°. The mixture is refluxed overnight, cooled to 0° and treated dropwise with 150 ml of methanol, followed by 30 ml of concentrated hydrochloric acid. The mixture is evaporated, again treated with 150 ml of methanol, warmed to 50° and evaporated. The resulting white solid is recrystallized from isopropanol containing a little methanol to afford the dl-1-(p-benzyloxyphenyl)-2-(3,3-diphenylpropylamino)-propane hydrochloride, melting at 187°–190°.

The starting material is prepared as follows: The stirring mixture of 45 g of dl-p-benzyloxyamphetamine, 81 g of 3,3-diphenylpropionic anhydride, 800 ml of benzene and 8 drops of concentrated sulfuric acid is refluxed for 18 hours. It is cooled, washed with aqueous sodium bicarbonate, water, dried and evaporated. The residue is recrystallized from ethyl acetate to afford the dl-1-(p-benzyloxyphenyl)-2-(3,3-diphenylpropionamido)-propane, melting at 121°–125°.

EXAMPLE 18

The solution of 20 g of dl-1-(p-benzyloxyphenyl)-2-(3,3-diphenylallylamino)-propane in 200 ml of 2-methoxyethanol is hydrogenated over 4 g of 10% platinum on charcoal at room temperature and atmospheric pressure until the hydrogen uptake ceases. The mixture is filtered, the filtrate evaporated and the residue taken up in the minimum amount of absolute ethanol. The solution is treated with an equimolar quantity of concentrated hydrochloric acid, the mixture evaporated and the residue recrystallized from isopropanol-methanol, to afford the dl-1-(p-benzyloxyphenyl)-2-(3,3-diphenylpropylamino)-propane hydrochloride, which is identical with that of Example 17.

The starting material is prepared as follows: The solution of 12 g of dl-p-benzyloxyamphetamine, and 10.4 g of β-phenyl-cinnamaldehyde in 300 ml of absolute ethanol is treated dropwse with the solution of 3 g of sodium borohydride in 6.7 ml of water while stirring. It is refluxed for 18 hours, concentrated to remove most of the ethanol and diluted with water. The mixture is extracted with ethyl acetate and the organic layer washed with brine, dried and evaporated, to yield the dl-1-(p-benzyloxyphenyl)-2-(3,3-diphenylallylamino)-propane; its maleate melts at 177°–178°.

EXAMPLE 19

The mixture of 6 g of dl-1-benzyloxyamphetamine, 7 g of 3,3-diphenylpropyl bromide, 100 ml of methyl ethyl ketone and 3.5 g of anhydrous potassium carbonate is refluxed for 3 days and evaporated. The residue is partitioned between water and ethyl acetate, the aqueous layer washed with ethyl acetate and the combined organic material washed with brine, dried and evaporated. The residue is taken up in isopropanol, treated with ethereal hydrogen chloride and the resulting solid recrystallized from isopropanol-methanol to afford the dl-1-(p-benzyloxyphenyl)-2-(3,3-diphenylpropylamino)-propane hydrochloride, which is identical with that of Example 17.

EXAMPLE 20

The mixture of 7.3 g of 2-(p-benzyloxyphenyl)-propyl bromide, 10 g of 3,3-diphenylpropylamine and 50 ml of dimethylformamide is heated to 100° for 2 hours and evaporated. The residue is suspended between water and diethyl ether, the aqueous layer extracted with diethyl ether and the combined extracts washed with brine, dried and evaporated. The residue is treated with ethereal hydrogen chloride and the resulting solid recrystallized from isopropanol-methanol, to afford the dl-1-(p-benzyloxyphenyl)-2-(3,3-diphenylpropylamino)-propane hydrochloride, which is identical with that of Example 17.

EXAMPLE 21

The mixture of 9.8 g of 2-(p-benzyloxyphenyl)-ethyl chloride, 16.9 g of 3,3-diphenylpropylamine and 50 ml of dimethylformamide is stirred at 100° for 18 hours. It is diluted with water, extracted with ethyl acetate, the extract washed with brine, dried and evaporated. The residual oil is dissolved in 40 ml of acetone and 5 g of oxalic acid are added, to yield the crystalline N-[2-(p-benzyloxyphenyl)ethyl]-3,3-diphenylpropylamine oxalate, melting at 225°–227° after recrystallization from dimethylacetamide.

EXAMPLE 22

To the solution of 30 g of 1-1-(4-hydroxyphenyl)-2-(3,3-diphenylpropylamino)propane in 150 ml of dimethylsulphoxide is added to the solution of 7.2 g of sodium hydroxide in 25 ml of water and the mixture is stirred at 60° for one-half hour. Thereafter 17.6 g of 3-cyanobenzyl bromide are added and the mixture is stirred overnight at ambient temperature. It is diluted with water, extracted with ethyl acetate, the extract washed with water, brine, dried and evaporated. The residual oil is redissolved in 800 ml of dry ethyl acetate and the solution treated with 4.2 ml of concentrated nitric acid. After standing in the cold crystals of l-1-[4-(3-cyanobenzyloxy)phenyl]-2-(3,3-diphenylpropylamino)-propane nitrate separate, melting at 140°–141°; $[M]_D = -47.3°$, (C=5 in methanol).

EXAMPLE 23

The mixture of 11 g of l-1-[4-(3-cyanobenzyloxy)-phenyl]-2-(3,3-diphenylpropylamino)propane, 50 ml of dimethylsulphoxide, 0.8 g of sodium hydroxide and 10 ml of water is stirred at 60° for 18 hours, cooled, diluted with water and extracted with ethyl acetate. The extract is washed with water and brine, dried and evaporated. The residual solid is recrystallized from toluene-cyclohexane, to afford the pure l-1-[4-(3-carbamoylbenzyloxy)-phenyl]-2-(3,3-diphenylpropylamino)-propane melting at 97°–100°; $[M]_D = -65.3°$ (C=5 in methanol).

EXAMPLE 24

When the racemic 1-(4-hydroxyphenyl)-2-(3,3-diphenylpropylamino)-propane is treated with 3-cyanobenzyl bromide as described in example 22, the dl-1-[4-(3-carbamoylbenzyloxy)-phenyl]-2-(3,3-diphenylpropylamino)-propane is obtained directly and isolated as its hemifumarate from isopropanol solution; it melts at 188°–190°.

130 g thereof are taken up in 2 lt of methanol-isopropanol (1:1) and 500 ml of 10 N aqueous sodium hydroxide are added. The mixture is warmed on a steam bath for one hour, then allowed to stir at room temperature until conversion to the sodium salt of the carboxylic acid is complete. The mixture is reduced in volume to remove organic solvents and then acidified under cooling with concentrated hydrochloric acid to yield the dl-1-[4-(3-carboxybenzyloxy)-phenyl]-2-(3,3-diphenylpropylamino)-propane, melting at 209°–212° after recrystallization from 2-(2-ethoxy-ethoxy)-ethanol.

EXAMPLE 25

The mixture of 9.0 g of 1-(4-benzyloxyphenyl)-2-amino-n-butane, 7.3 g of β-phenylcinnamaldehyde, 100 ml of absolute ethanol (100 ml) and 1 g of platinum oxide is shaken for 18 hours under three atmospheres of hydrogen. It is filtered, the filtrate treated with 15 ml of concentrated hydrochloric acid and evaporated. The residue is recrystallized from isopropanol, to afford the dl-2-(3,3-diphenylpropylamino)-1-(4-benzyloxyphenyl)-butane hydrochloride, melting at 160°–162°.

The starting material is prepared as follows: The mixture of 80 g of p-benzyloxybenzaldehyde, 100 ml of 1-nitro-propane and 5 ml of n-butylamine is placed in a reflux extractor filled with molecular sieves (type 5A), and refluxed for four hours. It is evaporated, the residue dissolved in diethyl ether containing some ethyl acetate and the solution stirred vigorously with a saturated sodium bisulphite solution for three hours. The inorganic layer is washed with ethyl acetate and the combined organic extracts washed with brine, dried and evaporated to afford the 1-(4-benzyloxyphenyl)-2-nitro-1-butene, which is used without further purification.

45 g thereof are dissolved in 500 ml of tetrahydrofuran and the solution added dropwise under nitrogen to the ice-cooled slurry of 30.4 g of lithium aluminum hydride in 500 ml of tetrahydrofuran. The mixture is stirred overnight, cooled with ice and treated with 200 ml of saturated aqueous ammonium chloride, followed by 1 lt more tetrahydrofuran. It is stirred for two hours at ambient temperature, filtered, the filter cake washed with ethyl acetate and the filtrate evaporated to afford the 1-(4-benzyloxyphenyl-2-amino-n-butane as an oil. It is dissolved in ethanol, the solution acidified with concentrated hydrochloric acid and the precipitate collected to yield the corresponding hydrochloride, melting at 222°–223°.

EXAMPLE 26

The mixture of 17.4 g of dl-p-benzyloxyamphetamine, 15.7 g of diphenylacetaldehyde, 200 ml of absolute ethanol and 0.5 g of platinum oxide is shaken under hydrogen at 3 atmospheres pressure for 72 hours. It is filtered, the filtrate acidified with concentrated hydrochloric acid and the whole evaporated. The residue is taken up in hot ethyl acetate and the crystalline d,l-1-(4-benzyloxyphenyl)-2-(2,2-diphenylethylamino)-propane hydrochloride collected and dried; it melts a 141°–144°.

EXAMPLE 27

The mixture of 11.1 g of dl-p-benzyloxyamphetamine hydrochloride, 11.2 g of 4,4-di-(4-fluorophenyl)-butyl chloride, 10.34 g of diisopropyl-ethylamine and 50 ml of dimethylformamide is stirred at 100° for 60 hours. It is evaporated, the residue taken up in benzene and the solution washed three times with water. The organic layer is dried, evaporated, the residue taken up in diethyl ether and the solution acidified with hydrogen chloride in isopropanol to afford the dl-1-(p-benzyloxyphenyl)-2-[4,4-di-(4-fluorophenyl)-butylamino]-propane hydrochloride, melting at 130°–133°.

EXAMPLE 28

7,775 ml of 1 molar borane in tetrahydrofuran are added to the solution of 805 g of 1-1-[4-(3-trifluoromethylbenzyloxy)phenyl]-2-(3,3-diphenylpropionamido)-propane in 6 lt of tetrahydrofuran over a period of 1 hour while stirring under nitrogen at 0°–5°. After addition, the mixture is allowed to warm to room temperature over 1 hour and the clear colorless solution is gently warmed to reflux. After refluxing for 6 hours, the mixture is allowed to stir overnight at room temperature. It is cooled again to 5° and 480 ml of water are added in a gentle stream over a period of 1 hour followed by 800 ml of concentrated hydrochloric acid. The reaction vessel is set for distillation and the solvent is removed at reduced pressure and at 40°. The residue is treated with 2 lt of methanol and the mixture evaporated again. The residue is triturated with 2 lt of diethyl ether for one hour, filtered off, washed with diethyl ether and dried, to yield 1,114 g of the 1-1-[4-(3-trifluoromethylbenzyloxy)-phenyl]-2-(3,3-diphenylpropylamino)-propane hydrochloride. It is dissolved in 8.9 lt of isopropanol at 80°, the solution filtered and the filtrate allowed to cool overnight in the ice box. The resulting suspension is filtered, the crystals obtained are washed with 500 ml of cold isopropanol and dried in vacuo at 80°. 580 g thereof are dissolved in 2.9 lt of boiling absolute ethanol and the clear solution is allowed to come to room temperature and stand overnight in the ice box. The crystals formed are filtered off, washed with 500 ml of cold absolute ethanol and dried in vacuo at 90° to yield said hydrochloride, melting at 153°–156°; $[M]_D = -44.8°$ (c=1 in methanol).

The starting material is prepared as follows: To the mixture of 592 g of 1-1-(4-hydroxyphenyl)-2-(3,3-diphenylpropionamido)-propane in 1.5 lt of dimethylsulfoxide, 118.4 g of sodium hydroxide and 295 ml of water, the solution of 352.5 g of 3-trifluoromethylbenzyl chloride in 310 ml of dimethylsulfoxide is added all at once. The resulting suspension is stirred under nitrogen at room temperature for 1 hour and at 55°–60° for 2 hours. Heating is removed and after another hour 6 lt of water are added in a gentle stream. After addition is complete, the suspension is stirred for 1 hour at 15°, filtered and the residue washed with 2 lt of water. It is dried in vacuo at 60° to yield 815 g of the 1-1-[4-(3-trifluoromethylbenzyloxy)-phenyl-2-(3,3-diphenylpropionamido)-propane, melting at 110°–113°; $[M]_D = +25.87°$ (c=1 in methanol).

Alternatively, this starting material can be prepared in the following way: The mixture of 50.5 g of 1-p-(3-trifluoromethylbenzyloxy)amphetamine, 81.0 g of 3,3-diphenylpropionic anhydride, 800 ml of benzene and 8 drops of concentrated sulfuric acid is stirred at reflux for 18 hours. It is cooled, washed with aqueous sodium bicarbonate, then water, dried and evaporated. The residual solid is washed with water and dried to yield the above amide obtained by said alternate route.

EXAMPLE 29

The mixture of 16 g of 1-1-(4-hydroxyphenyl)-2-(3,3-diphenylpropylamino)propane, 50 ml of dimethylsulfoxide, 3.4 g of sodium hydroxide and 10 ml of water is stirred at 60° for one hour and then 8.7 g of 3-trifluoromethylbenzyl chloride are added. The mixture is stirred overnight at ambient temperature, treated with 300 ml of N aqueous sodium hydroxide and extracted with methylene chloride. The extract is dried, evaporated and the residue dissolved in 50 ml of isopropanol. The solution is treated dropwise with isopropanolic hydrogen chloride until the mixture is acidic. It is allowed to stand in the refrigerator overnight, the crystals formed are collected, washed with cold isopropanol and recrystallized from absolute ethanol to afford the 1-1-[4-(3-trifluoromethylbenzyloxy)-phenyl]-2-(3,3-diphenylpropylamino)-propane hydrochloride, melting at 153°–156°, $[M]_D = -44.7°$ (C=1% in methanol).

The starting material is prepared as follows: The mixture of 23 g of 1-1-(4-hydroxyphenyl)-2-aminopropane, 31.2 g of diphenylacrolein, 150 ml of anhydrous ethanol and 4 g of 10% palladium on carbon is hydrogenated at 3.3 atmospheres for six hours. It is filtered, the filtrate evaporated, the residue dissolved in 400 ml of isopropanol and 12.5 ml of concentrated hydrochloric acid are added. After overnight refrigeration the resulting precipitate is collected, washed with isopropanol and diethyl ether and dried, to afford 1-1-(4-hydroxyphenyl)-2-(3,3-diphenylpropylamino)propane hydrochloride melting at 244°–247°, $[M]_D = -35.1°$ (C=5% in methanol). The free base is liberated therefrom as illustrated in previous examples.

EXAMPLE 30

The mixture of 23.6 g of 1-p-(3-trifluoromethylbenzyloxy)-amphetamine, 15.8 g of β-phenylcinnamaldehyde and 100 ml of dry benzene is stirred at reflux in an apparatus containing a water separator, until no more water is collected. The solution is evaporated, the residue taken up in 100 ml of dry tetrahydrofuran and added dropwise under nitrogen to a cooled, stirred slurry of 8.7 g of lithium aluminum hydride in 150 ml of dry tetrahydrofuran. The whole is stirred at ambient temperature overnight, then cooled with ice and treated cautiously with saturated aqueous ammonium chloride until the residual hydride is destroyed. The mixture is filtered and both the filtrate and precipitate extracted with chloroform. The combined extracts are dried, evaporated to dryness and the residue is dissolved in dry diethyl ether and treated with an equimolar quantity of methanesulfonic acid. The mixture is refrigerated overnight and the crystals formed are collected, washed with diethyl ether and dried in a high vacuum at room temperature to afford the 1-1-[4-(3-trifluoromethylbenzyloxy)-phenyl]-2-(3,3-diphenylpropylamino)-propane methanesulfonate melting at 100° to 101°; $[M]_D = -38.4°$, (C=5% in methanol).

Alternatively, the crude free base is taken up in methanol and the solution treated with an equimolar quantity of l-dibenzoyltartaric acid hydrate and allowed to crystallize at room temperature. The resulting salt is triturated with warm methanol, collected and dried to afford the 1-1-[4-(3-trifluoromethylbenzyloxy)-phenyl]-2-(3,3-diphenylpropylamino)propane l-dibenzoyltartrate, melting at 184°–185°, $[M]_D = -349°$ (C=0.5% in methanol).

EXAMPLE 31

To the solution of 5.27 g of dl-1-[4-(3-trifluoromethylbenzyloxy)phenyl]-2-(3,3-diphenylpropylamino)-propane in 50 ml of methanol is added 3.86 g of l-dibenzoyltartaric acid hydrate in 50 ml of methanol. The mixture is allowed to stand for 6 hours and then water is added dropwise to the cloud point. On scratching the inside of the flask near the surface of the solution crystallization is initiated. After standing for several days at room temperature, the crystals are collected and recrystallized first from methanol-water and then from absolute methanol to afford the l-dibenzoyltartrate salt described in Example 30; m.p. 182°-183°, [M]$_D$=−330° (C=0.5% in methanol).

The starting material may be prepared according to Example 13, in which dl-1-(4-hydroxyphenyl)-2-(3,3-diphenylpropylamino)-propane (prepared as described by Ehrhart et al., U.S. Pat. No. 3,152,173) is substituted for its levorotartory antipode. In this instance, the isolated free base is taken up in isopropanol and the crystals which form are recrystallized from isopropanol, to afford the pure dl-1-[4-(3-trifluoromethylbenzyloxy)-phenyl]-2-(3,3-diphenylpropylamino)-propane maleate melting at 135° to 137°.

EXAMPLE 32

The solution of 2 g of 1-1-[4-(3-trifluoromethylbenzyloxy)-phenyl]-2-(3,3-diphenylallylamino)-propane in 30 ml of 2-methoxyethanol is hydrogenated in the presence of 0.6 g of 10% platinum on charcoal at room temperature and pressure until the uptake of hydrogen ceases. The mixture is filtered, the filtrate evaporated and the residue taken up in the minimum amount of isopropanol. The solution is treated with hydrogen chloride in isopropanol to obtain the identical product as described in Example 29.

The starting material is prepared as follows: the mixture of 1.5 l of l-p-hydroxyamphetamine, 0.84 g of 57% sodium hydride in mineral oil and 50 ml of dry diemthylformamide is treated with 20 g of m-trifluoromethylbenzyl chloride under nitrogen and the whole is stirred at ambient temperature for 42 hours. The mixture is poured into 500 ml of water and extracted several times with diethyl ether. The extract is dried and evaporated to afford the l-p-(3-trifluoromethylbenzyloxy)-amphetamine.

The solution of 13.5 g thereof, 10.4 g of β-phenylcinnamaldehyde and 300 ml of ethanol is treated dropwise with the solution of 3 g of sodium borohydride in 6.7 ml of water while stirring. It is heated overnight at reflux, concentrated to remove most of the ethanol and diluted with water. The mixture is extracted with ethyl acetate and the organic layer washed with brine, dried and evaporated to yield the 1-1[4-(3-trifluoromethylbenzyloxy)-phenyl]-2-(3,3-diphenylallylamino)-propane.

EXAMPLE 33

The mixture of 6.75 g of -p-3(trifluoromethylbenzyloxy)-amphetamine, 7.0 g of 3,3-diphenylpropyl bromide, 100 ml of methyl ethyl ketone and 3.5 g of anhydrous potassium carbonate is heated at reflux for 3 days and then evaporated. The residue is suspended in ethyl acetate and water and the water layer again extracted with ethyl acetate. The organic extracts are washed with brine, dried and evaporated. The residue is taken up in isopropanol and converted into its hydrochloride salt, as described in Example 29, which is identical with that described therein.

EXAMPLE 34

The mixture of 11.8 g of l-p-(3-trifluoromethylbenzyloxy)-amphetamine, 8.0 g of β-phenylcinnamaldehyde and 50 ml of dry benzene is stirred at reflux in an apparatus containing a water separtor until no more water is collected. The solution is evaporated, the residue dissolved in 300 ml of absolute ethanol and the solution treated with 3 g of 10% platinum on charcoal. The suspension is hydrogenated at 3 atmospheres at room temperature until no more hydrogen is taken up. It is filtered, the filtrate evaporated, the residue taken up in isopropanol and converted to its hydrochloride as described in Example 29, to yield the hydrochloride identical with the product obtained therein.

EXAMPLE 35

The mixture of 18.3 g of 1-(4-hydroxyphenyl)-2-(3,3-diphenylpropylamino)-propane, 100 ml of dimethylsulfoxide and 5.29 ml of 10 N-aqueous sodium hydroxide is stirred at room temperature for one hour, combined with 9.66 g of 4-t-butylbenzyl chloride and stirred 18 hours longer. It is poured into 1,000 ml of water, extracted twice with 500 ml of methylene chloride, the extract dried and evaporated at about 60°. The residue is taken up in isopropanol, the solution acidified with 5% isopropanolic maleic acid, the precipitate collected and recrystallized from isopropanol-diethyl ether, to yield the 1-[4-(4-t-butylbenzyloxy)-phenyl]-2-(3,3-diphenylpropylamino)-propane maleate melting at 132°-134°.

The starting material is prepared as follows: the mixture of 246.3 g of p-methoxyphenylacetone, 317 g of 3,3-diphenylpropylamine and 1,000 ml of anhydrous ethanol is hydrogenated at 20° and 3.4 atm. over 5 g of platinum oxide. After the theoretical amount of hydrogen has been absorbed (ca 4,000 ml), the mixture is filtered and the filtrate evaporated at 60°, to yield the 1-(4-methoxyphenyl)-2-(3,3-diphenylpropylamino)-propane as an oil.

The mixture of 438 g thereof, 2,000 ml of 48% hydrobromic acid and 2,000 ml of glacial acetic acid is refluxed for 18 hours and poured into 7,500 ml of water. The mixture is stirred for 2 hours at 20°, filtered, the residue dissolved in 6,000 ml of 2 N aqueous sodium hydroxide and the solution washed with ethyl acetate. It is neutralized with acetic acid, the precipitate formed collected, dissolved in the minimum amount of ethyl acetate and the solution combined with 116 g of maleic acid, to yield the 1-(4-hydroxyphenyl)-2-(3,3-diphenylpropylamino)-propane maleate melting at 184°-186°.

The mixture of 25 g thereof and 500 ml of saturated aqueous sodium bicarbonate is extracted thrice with 250 ml of ethyl acetate. The combined extracts are dried and evaporated at 60° to yield the corresponding free base.

EXAMPLE 36

Preparation of 1,000 capsules each containing 50 mg of the active ingredient

| Formula: | |
|---|---|
| p-1-[4-(3-trifluoromethylbenzyloxy)-phenyl]-2-(3,3-diphenylpropylamino)-propane hydrochloride | 50.00 g |
| Modified corn starch | 5.00 g |
| Lactose | 143.75 g |
| Magnesium stearate | 1.00 g |
| Surfactant | 0.25 g |

Procedure:

All the powders are passed through a screen with openings of 0.6 mm. Then the drug substance is mixed first with the magnesium stearate and surfactant, whereupon the starch and lactose are added and mixed until

I claim:

1. A compound corresponding to the formula

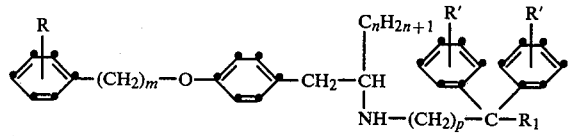

wherein R is hydrogen, m- or p-(chloro or trifluoromethyl), each of $R_1$ and R' are hydrogen, each of m and n is the integer 1 and p is the integer 2, or a therapeutically useful acid addition salt thereof.

2. A compound as claimed in claim 1 and being the levorotatory optical antipode thereof.

3. A compound as claimed in claim 1 and being the d,l-1-[4-(3-trifluoromethylbenzyloxy)-phenyl]-2-(3,3-diphenylpropylamino)-propane, or a therapeutically useful acid addition salt thereof.

4. A compound as claimed in claim 3 and being the levorotatory hydrochloride thereof.

5. A pharmaceutical composition for the treatment of hypertension comprising an antihypertensive effective amount of a compound as claimed in claim 1, together with a pharmaceutical excipient.

6. A method of treating hypertension in mammals, which consists in administering to said mammals enterally or parenterally an antihypertensive effective amount of a composition as claimed in claim 5.

* * * * *

UNITED STATES PATENT AND TRADEMARK OFFICE
CERTIFICATE OF CORRECTION

PATENT NO. : 4,329,367
DATED : May 11, 1982
INVENTOR(S) : John E. Francis

It is certified that error appears in the above--identified patent and that said Letters Patent are hereby corrected as shown below:

In the abstract column 2, line 51 reads:

cause cause sedation. ......

Should read:

-- which cause sedation. ..... --

Column 4, line 67 reads:

derivatives of the acid $HOCC[C_pH_{2p}-1-v]$........

Should read:

-- derivatives of the acid $HOOC[C_pH_{2p}-1-v]$...... --

UNITED STATES PATENT AND TRADEMARK OFFICE
CERTIFICATE OF CORRECTION

PATENT NO. : 4,329,367  Page 2 of 5
DATED : May 11, 1982
INVENTOR(S) : John E. Francis It is certified that error appears in the above-identified patent and that said Letters Patent are hereby corrected as shown below:

In the abstract column 4, line 68 reads:

preparing Iva and reducing in any resulting amide the

Should read:

-- preparing IVa and reducing in any resulting amide the --

Example 1, column 7, line 38 reads:

....... chloide until the remaining should read:

-- ...... chloride until the remaining --

UNITED STATES PATENT AND TRADEMARK OFFICE
CERTIFICATE OF CORRECTION

PATENT NO. : 4,329,367
DATED : May 11, 1982
INVENTOR(S) : John E. Francis

It is certified that error appears in the above-identified patent and that said Letters Patent are hereby corrected as shown below:

Examples 5, column 8, line 68 reads:

vigorously at refux ......

Should read:

-- vigorously at reflux ...... --

Example 6, column 9, line 35 reads:

...... [M]HD D=35.1 (5% in

Should read:

....... $[M]_D = 35.1°$ (5% in --

UNITED STATES PATENT AND TRADEMARK OFFICE
CERTIFICATE OF CORRECTION

PATENT NO. : 4,329,367
DATED : May 11, 1982
INVENTOR(S) : John E. Francis

It is certified that error appears in the above-identified patent and that said Letters Patent are hereby corrected as shown below:

Example 12, column 12, line 46 reads:

d,p-1-...........

Should read:

d,l-1- .........

Example 18, column 14, line 46 reads:

....... dropwse ......
Should read:
-- ..... dropwise ...... --

Example 33, column 19, line 50 reads:

......... -p-3(trifluoromethylben-

Should read:

-- ....... 1-p-3(trifluoromethylben- --

UNITED STATES PATENT AND TRADEMARK OFFICE
CERTIFICATE OF CORRECTION

PATENT NO. : 4,329,367
DATED : May 11, 1982
INVENTOR(S) : John E. Francis

It is certified that error appears in the above-identified patent and that said Letters Patent are hereby corrected as shown below:

Example 34, column 19, line 66 reads:

......... separtor until no more

Should read:

-- ....... separator until no more

Example 36, column 20, line 57 reads:

p-1-[4-(3-trifluoromethylbenzyloxy)-

Should read:

1-1-[4-(3-trifluoromethylbenzyloxy)-

Signed and Sealed this

Twenty-second Day of February 1983

[SEAL]

Attest:

GERALD J. MOSSINGHOFF

*Attesting Officer*     *Commissioner of Patents and Trademarks*